(12) United States Patent
Syrek et al.

(10) Patent No.: US 10,675,452 B2
(45) Date of Patent: Jun. 9, 2020

(54) MICRO-NEEDLE DEVICE (71) Applicant: 3M INNOVATIVE PROPERTIES COMPANY, St. Paul, MN (US)

(72) Inventors: Andreas Syrek, Munich (DE); Marc Peuker, Schoendorf (DE); Mathias Bertl, Wildsteig (DE); Martin Preininger, Bavaria (DE); Emir Jelovac, Munich (DE); Ryan P. Simmers, Fargo, ND (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 24 days.

(21) Appl. No.: 15/124,400

(22) PCT Filed: Mar. 5, 2015

(86) PCT No.: PCT/US2015/018897
§ 371 (c)(1),
(2) Date: Sep. 8, 2016

(87) PCT Pub. No.: WO2015/138206
PCT Pub. Date: Sep. 17, 2015

(65) Prior Publication Data
US 2017/0173316 A1      Jun. 22, 2017

Related U.S. Application Data

(60) Provisional application No. 61/950,420, filed on Mar. 10, 2014.

(51) Int. Cl.
*A61M 37/00* (2006.01)
*A61B 5/00* (2006.01)

(52) U.S. Cl.
CPC ........ *A61M 37/0015* (2013.01); *A61M 37/00* (2013.01); *A61B 5/685* (2013.01);
(Continued)

(58) Field of Classification Search
CPC .............. A61M 37/0015; A61M 37/00; A61M 2037/0023; A61M 2037/003;
(Continued)

(56) References Cited

U.S. PATENT DOCUMENTS 2,768,623 A * 10/1956 Marchand ............. A61M 5/282
604/204
4,072,249 A * 2/1978 Ekenstam ............. A61M 5/282
222/107
(Continued)

FOREIGN PATENT DOCUMENTS

WO      WO 94/23777      10/1994
WO      WO 2006-016364    2/2006

OTHER PUBLICATIONS

International Search Report for PCT International Application No. PCT/US2015/018897 dated Aug. 6, 2015, 4 pages.

*Primary Examiner* — Nilay J Shah
(74) *Attorney, Agent, or Firm* — 3M Innovative Properties Company (57) ABSTRACT

A micro-needle device for delivering a dental local anesthetic that includes a micro-needle array and a hollow spheroid shaped container. The micro-needle array has a base and two or more elongate micro-needles. The elongate micro-needles have an interior surface defining an opening through the elongate micro-needle and the base has a first major surface and a second major surface through which the opening of the elongate micro-needle passes to provide a passage across the base. The hollow spheroid shaped container includes an inside surface, where the first major surface of the base and the inside surface of the hollow spheroid shaped container define a volume that is in fluid connection with each opening of the two or more of the elongate micro-needle. This allows the dental local anes-
(Continued)

thetic to flow from the volume of the micro-needle device through the opening of the two or more of the elongate micro-needle.

11 Claims, 6 Drawing Sheets

(52) U.S. Cl.
CPC .............. *A61M 2037/003* (2013.01); *A61M 2037/0023* (2013.01); *A61M 2037/0046* (2013.01); *A61M 2037/0061* (2013.01); *A61M 2210/0625* (2013.01); *A61M 2210/0631* (2013.01)

(58) Field of Classification Search
CPC .............. A61M 5/2425; A61M 5/282; A61B 5/150984; A61B 5/685
See application file for complete search history.

(56) References Cited

U.S. PATENT DOCUMENTS

| | | | | |
|---|---|---|---|---|
| 4,181,223 | A * | 1/1980 | Millet | A61M 5/002 206/365 |
| 5,697,919 | A * | 12/1997 | Kinoshita | A61M 5/1424 604/185 |
| 6,190,367 | B1 | 2/2001 | Hall | |
| 6,611,707 | B1 * | 8/2003 | Prausnitz | A61B 5/14514 604/21 |
| 7,959,902 | B1 * | 6/2011 | Postlewaite | A46B 5/04 132/308 |
| 8,398,397 | B2 | 3/2013 | Fischer | |
| 2002/0188245 | A1 | 12/2002 | Martin | |
| 2007/0083156 | A1 * | 4/2007 | Muto | A61M 1/285 604/93.01 |
| 2012/0258419 | A1 | 10/2012 | Brundidge, III | |
| 2013/0006216 | A1 | 1/2013 | Taylor | |
| 2013/0110053 | A1 | 5/2013 | Yoshino | |

* cited by examiner

MICRO-NEEDLE DEVICE

FIELD OF THE DISCLOSURE

The disclosure relates to a medical device and in particular to a medical device having micro-needles.

BACKGROUND ART

Needles sometimes need to be used for injections during medical procedures. The sight, thought and/or feeling of a needle can cause fear in the patient. This fear, or phobia, of needles is known as needle phobia.

Depending upon the degree of needle phobia, a patient can display a wide variety of symptoms. For example, a patient with needle phobia can have anxiety, a panic attack, an elevated blood pressure and/or an elevated heart rate knowing that a needle may or will be used in their medical procedure. In extreme cases the patient can faint due to a vasovagal reflex reaction. This leads to an unsafe situation for both the patient and the medical personnel. Other reactions of patients with needle phobia can include avoiding medical treatment if they know or believe a needle will be used. In extreme cases, some patients will avoid all medical care. This fear of needles can also be associated with the sight of a syringe.

In dentistry, a syringe fitted with a needle is often times used to deliver an anesthetic to the patient. The needle and syringe are inserted at least partially into the patient's mouth, where the needle is inserted into the gingiva and/or other tissues (e.g., oral mucosa) in order to deliver a local anesthetic. Using a local anesthetic can help to decrease intraoperative and postoperative pain, decrease the amount of general anesthetics used in the operating room, increase the patient cooperation during the procedure. Often times the injection is more painful and traumatic than the actual procedure.

Therefore, there is a need in the art for a suitable device for injecting a local anesthetic that does not use a traditional needle and syringe configuration, which configurations are well known to cause issues with many patients.

SUMMARY OF THE DISCLOSURE

The present disclosure provides a device for delivering a dental local anesthetic that does not use a traditional needle and syringe configuration. For example, the micro-needle device of the present disclosure does not include a plunger. The present disclosure provides a micro-needle device for delivering a dental local anesthetic that includes a micro-needle array having a base and two or more of an elongate micro-needle, the elongate micro-needle having an interior surface defining an opening through the elongate micro-needle and the base having a first major surface and a second major surface through which the opening of the elongate micro-needle passes to provide a passage across the base; and a hollow spheroid shaped container, where the first major surface of the base and an inside surface of the hollow spheroid shaped container define a volume that is in fluid connection with each opening of the two or more of the elongate micro-needle to allow the dental local anesthetic to flow from the volume of the micro-needle device through the opening of the two or more of the elongate micro-needle. The base of the micro-needle array can have a disk-shape.

The hollow spheroid shaped container has a wall providing the inner surface and an outer surface, where the outer surface of the wall can include a volumetric scale marker. The volumetric scale marker can be used to determine the approximate amount of the volume that has flowed from the volume of the micro-needle device through the opening of the two or more of the elongate micro-needle. An example of the volumetric scale marker can include a transition in a thickness of the wall, where the transition in the thickness of the wall can follow along a latitudinal portion of the hollow spheroid shaped container. The hollow spheroid shaped container can have a volume of about one milliliter. The outer surface of the hollow spherical container may also include a pressure sensitive adhesive for retaining the micro-needle device on a user's finger.

The wall of the hollow spheroid shaped container is formed of a polymer that elastically deforms under a compressive force applied to the outer surface of the hollow spheroid shaped container. So, the outer surface of the hollow spherical container can, under the compressive force applied to the outer surface of the hollow spheroid shaped container, changes from having a convex shape to having a concave shape.

The micro-needle device can further include a removable cover positioned over at least a portion of the base and the two or more of the elongate micro-needle. The second major surface of the base can includes a compressible coat surrounding the micro-needles, the compressible coat formed from a foamed elastic material and having an outer surface, where the compressible coat changes shape under a compressive force to allow the micro-needles to extend beyond the outer surface of the compressible coat. Each micro-needle includes a tip that does not extend above the outer surface of the compressible coat.

BRIEF DESCRIPTION OF THE FIGURES

The Figures may not be to scale.

DETAILED DESCRIPTION OF THE DISCLOSURE

The micro-needle device of the present disclosure may be used to inject a local anesthetic without using a traditional needle and syringe configuration. As disclosed herein, the micro-needle device has a non-medical device appearance, but yet enables the delivery of a dental local anesthetic to the oral tissues of a patient. The micro-needle device of the present disclosure provides a micro-needle array having a low profile that allows for discrete handling and insertion into the patients mouth. As such, a patient having needle phobia may be less likely to react negatively and/or be more willing to undergo a dental procedure because the traditional needle and syringe configuration will not be used.

The micro-needle device of the present disclosure does not include a plunger.

As used herein, "a," "an," "the," "at least one," and "one or more" are used interchangeably. The term "and/or" means one, one or more, or all of the listed items. The recitations of numerical ranges by endpoints include all numbers subsumed within that range (e.g., 1 to 5 includes 1, 1.5, 2, 2.75, 3, 3.80, 4, 5, etc.).

As recited herein, all numbers can be considered to be modified by the term "about."

The figures herein follow a numbering convention in which the first digit or digits correspond to the drawing figure number and the remaining digits identify an element or component in the drawing. Similar elements or components between different figures may be identified by the use of similar digits. For example, 214 may reference element "14" in FIG. 2, and a similar element may be referenced as 314 in FIG. 3. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense.

Referring now to FIGS. 1A-1D, there is shown an embodiment of a micro-needle device 100 for delivering a dental local anesthetic. The micro-needle device 100 includes a micro-needle array 102 having a base 104 and two or more of an elongate micro-needle 106, and a hollow spheroid shaped container 108. The elongate micro-needle 106 has an interior surface 110 defining an opening 112 through the elongate micro-needle 106. The base 104 has a first major surface 114 and a second major surface 116 through which the opening 112 of the elongate micro-needle 106 passes to provide a passage across the base 104.

The hollow spheroid shaped container 108 includes a wall 118 that provides an inner surface 120 and an outer surface 122. The first major surface 114 of the base 104 and the inner surface 120 of the hollow spheroid shaped container 108 define a volume 124. The volume 124 is in fluid connection with each opening 112 of the two or more of the elongate micro-needle 106 to allow the dental local anesthetic to flow from the volume 124 of the micro-needle device 100 through the opening 112 of the two or more of the elongate micro-needle 106 when a compressive force is applied to the wall 118 of the hollow spheroid shaped container 108.

A problem with traditional needle structures is that the connector of the needle (e.g., a Luer connector) is aligned with the needle along the direction through which the force is applied to insert the needle into the patient. In order to apply this force and inject the substance into the patient a syringe is joined to the needle. Once the syringe is joined to the needle the structure is so long that the patient could not help noticing it. The sight of this very long structure with its needle can be of great concern for those people with needle phobia.

In contrast to traditional needle and syringe structure, the micro-needle array 102 of the present disclosure has a disk-shape. As illustrated, the base 104 has an exterior surface 126 that defines the disk-shape of the micro-needle array 102. As illustrated, the exterior surface 126 includes the first major surface 114, the second major surface 116 and a sidewall 128 that extends between the first major surface 114 and the second major surface 116 of the disk-shaped base 104. The exterior surface 126 of the base 104 provides a relatively large surface on which the doctor can both hold and apply force to the micro-needle device 100 to insert the micro-needles 106 in the oral tissue of the patient. One advantage of this disk-shape is that the doctor can discretely hold the micro-needle array 102 in a position that also allows them to use the micro-needle device 100.

The first major surface 114 and the second major surface 116 of the base 104 of the micro-needle array 102, in the disk-shape, can have a diameter of 4 millimeters (mm) to 15 mm and the sidewall 128 can have a height of 0.5 mm to 8 mm. Preferably, the base 104 of the micro-needle array 102, in the disk-shape can, have a diameter of 5 mm to 10 mm, and a height of 1 mm to 6 mm. Most preferably, the base 104 of the micro-needle array 102, in the disk-shape can, can have a diameter of 6 mm to 8 mm, and a height of 2 mm to 4 mm.

Figure 1A:
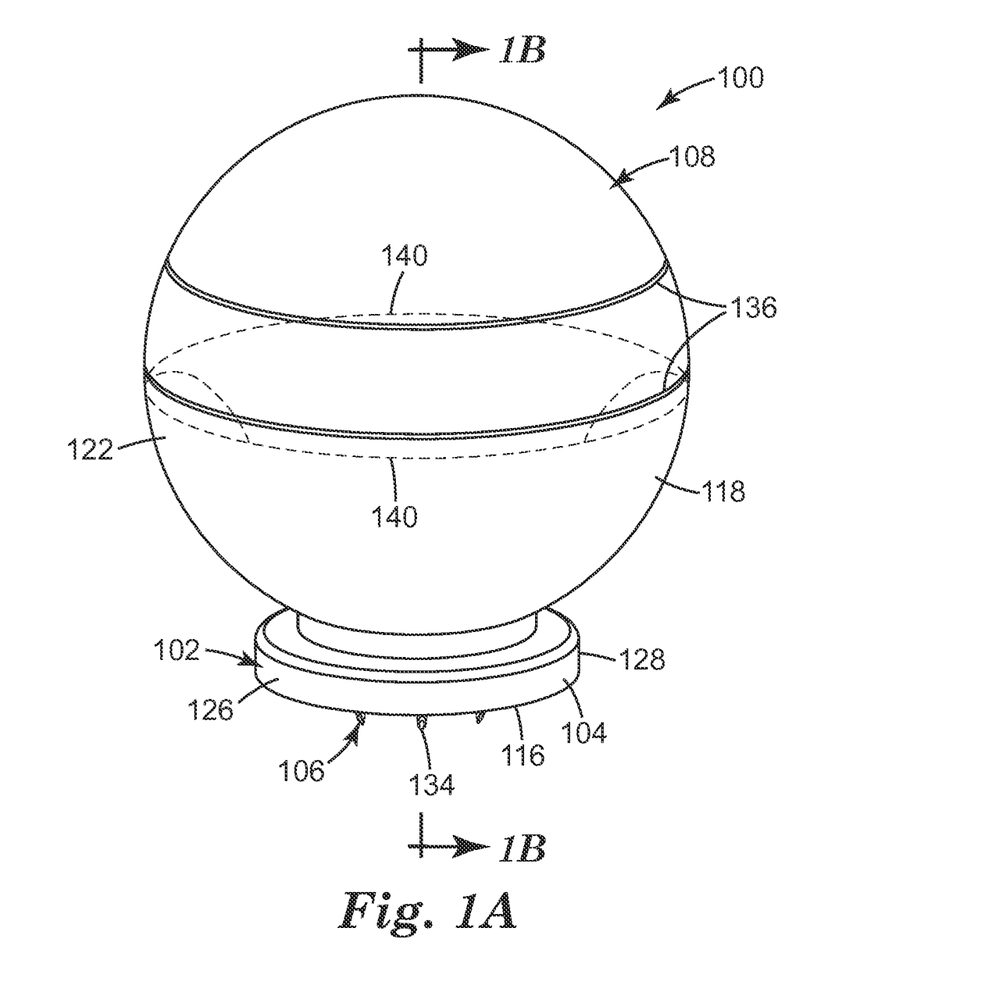
FIG. 1A is a perspective view of a micro-needle device according to an embodiment of the present disclosure.
Figure 1B:
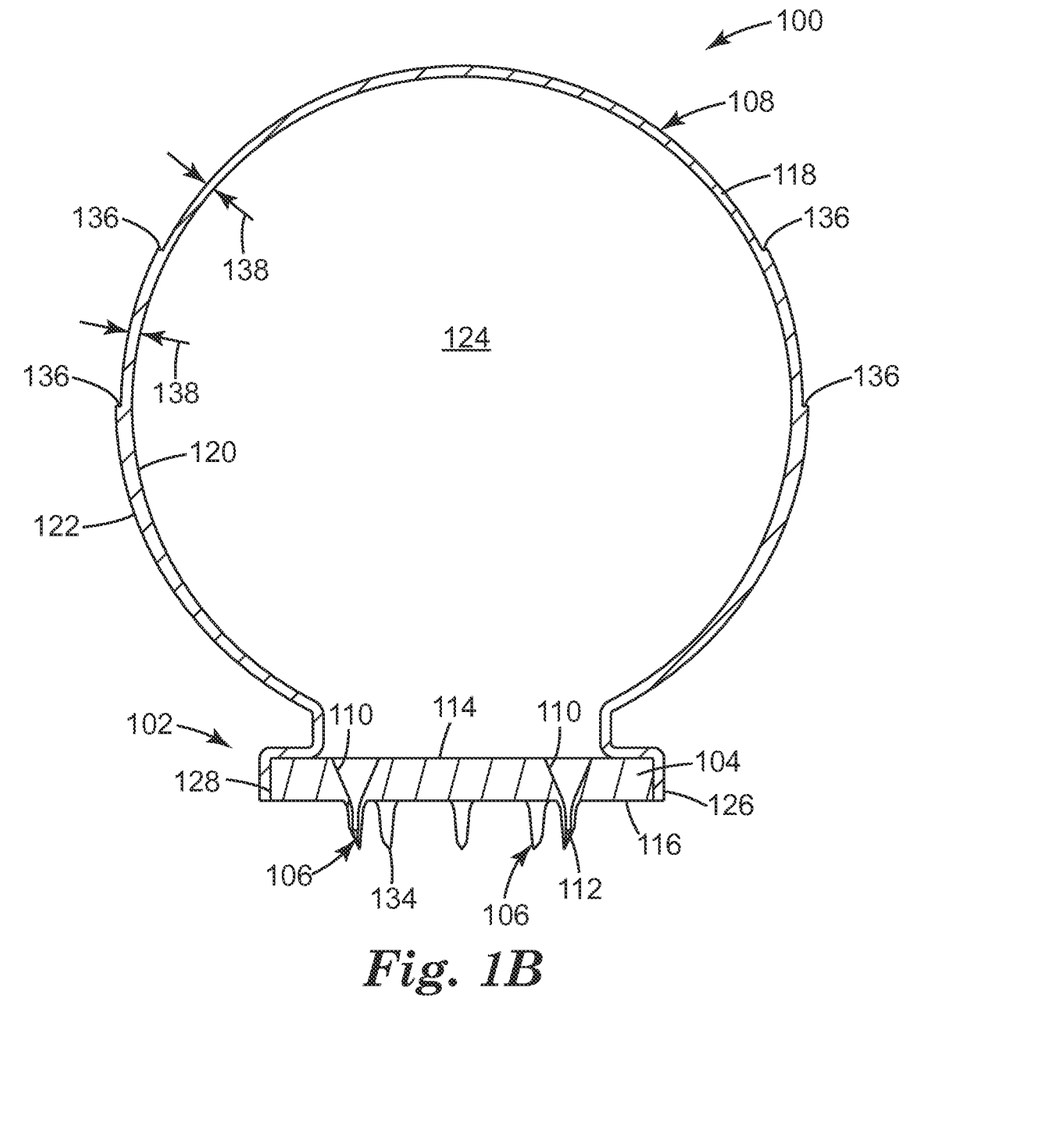
FIG. 1B is a cross sectional view of the micro-needle device taken along lines 1B in FIG. 1A.
Figure 1C:
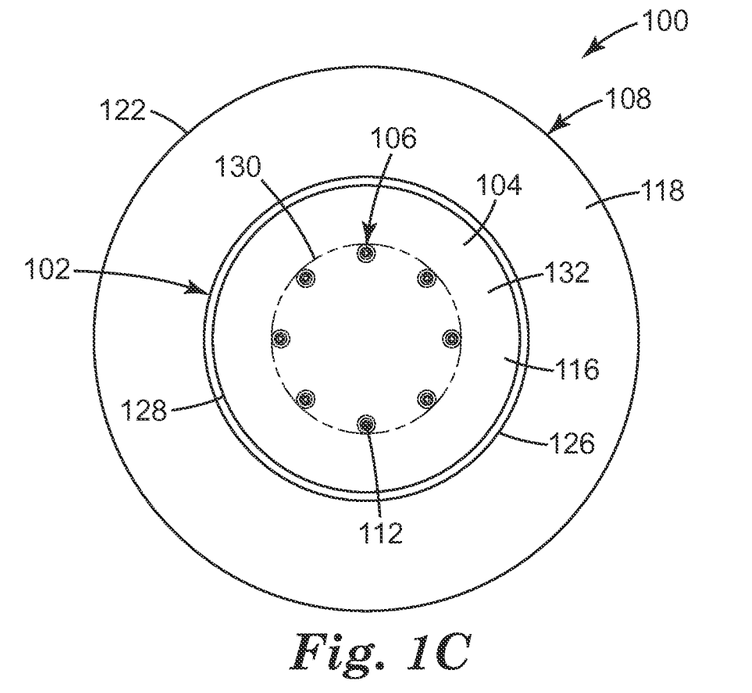
FIG. 1C is a plan view of the micro-needle device of FIG. 1A taken along line 1C in FIG. 1A.

The base 104 of the micro-needle array 102 has 6 to 18 micro-needles 106. As illustrated in FIG. 1C, micro-needles 106 extend from the second major surface 116 of the base 104 to define an boundary 130 (shown with a broken line in FIG. 1C) to define an infiltration area 132 (the area that extends from the boundary 130 to the sidewall 128 of the base 104). As illustrated, the micro-needles 106 of the micro-needle array 102 have a pattern. For example, the micro-needles 106 can uniformly arranged in a circular pattern to help define the infiltration area 132, as illustrated in FIG. 1C. In this embodiment, the circular pattern is centric relative the geometric center of the second major surface 116 of the base 104. If desired, the pattern of the micro-needles 106 can be either centric or eccentric relative the geometric center of the second major surface 116 of the base 104. Other patterns for the micro-needles 106 include, but are not limited to, elliptical, oval or polygonal, where the patterns can be eccentric or centric relative the geometric center of the second major surface 116 of the base 104.

The width of the infiltration area 132 defined by the pattern of the micro-needles 106 can be from 2 mm to 10 mm. So, when the micro-needles 106 are arranged in a circular pattern the infiltration area can be from 3.14 mm$^2$ to 78.5 mm$^2$. Preferably, the pattern of the micro-needles 106 provides a width (e.g., a diameter) of the infiltration area of 6 mm. Micro-needles 106 can be spaced, on center of their longitudinal axis from each other, in a range from 1 mm to 5 mm. Preferably, the micro-needles 106 can be spaced, on center of their longitudinal axis from each other, in a range from 1.5 mm to 2 mm.

As for the micro-needles 106, they can have a tip 134 spaced from the second major surface 116 of the base 104, where the tip 134 has a bevel. Examples of such bevels include, but are not limited to, a true short bevel, a short bevel or a standard bevel as are known. The elongate micro-needles 106 also have an outer diameter in a range of 100 micrometer (μm) to 400 μm. The micro-needles 106 also have a length in a range from 500 μm to 1500 μm. The micro-needles 106 of the micro-needle array 102 can all have the same approximate length so that the tip 134 of micro-needles 106 are all approximately on a common plane. Alternatively, micro-needles 106 of the micro-needle array 102 can have different lengths so that the tips 134 of micro-needles 112 are not all approximately on a common plane.

It is appreciated that other flat thin shapes may also be used instead of a disk-shape for the micro-needle array 102. For example, the micro-needle array 102 may have, as viewed perpendicular to the first major surface 114 and the second major surface 116, an oval shape, an elliptical shape or a polygon shape. The exact shape of the micro-needle array 102 can be determined based on the desired use and location of the use for the micro-needle device 100.

The different components of the micro-needle array 102 can be formed from a polymeric material. For example, the micro-needle array 102 can be made of a polymer selected from the group consisting of aromatic polyester polymers or polycarbonate polymers. Examples of aromatic polyester polymers include liquid crystal polymers (partially crystalline aromatic polyesters based on p-hydroxybenzoic acid and related monomers), such as those sold under the trade designator "Siveras LX" (Toray), "Sumikasuper" (Sumitomo), "Titan" (DuPont), "Vectra" (Celanese), "Xydar" (Solvay Specialty Polymer) or "Zenite" (Celanese). Suitable examples of polycarbonate polymers include those of medical grade that comply with ISO 10993-1 and/or USP Class VI standards.

Examples of suitable polymers for the hollow spheroid shaped container include polymers selected from the group consisting of high density polyethylene (HDPE), low density polyethylene (LDPE), polypropylene (PP), polyethylene terephthalate (PET), brominated butyl rubber or acrylonitrile-methyl acrylate copolymer. An example of the acrylonitrile-methyl acrylate copolymer includes BAREX®. The hollow spheroid shaped container can be formed from a single layer of the aforementioned polymers. It is also possible that the hollow spheroid shaped container can be formed from a multilayer structure of the aforementioned polymers. For example, such multilayer structures can include two or more layers of different polymers such as PP, HDPE, LDPE and/or PET. A metal may also be used in the multilayer structure, for example aluminum can be used as one or more layers with the multilayer structure as discussed herein. A coating can also be provided on the single or multilayer structure, where the coating can be formed with ethyl-vinyl-alcohol, silicone oxide and/or aluminum oxide compounds.

The different components of the micro-needle device 100 can be formed as separate structures or different combinations of the components can be formed from a single piece of the polymeric material. For example, the base 104 and the micro-needles 106 of the micro-needle array 102 can be formed as a first piece of the micro-needle device 100 in an injection molding process, where the openings 112 can directly be injection molded or a laser can be used to form (e.g., drill) the openings 112 of the micro-needles 106. Other techniques for forming the openings 112 are possible, including using a water jet or a plasma cutting operation to form the openings 112.

Similarly, the hollow spheroid shaped container 108 can be formed as a second piece of the micro-needle device 100 in an injection molding process or a blow-molding process. The two pieces of the micro-needle device 100 can then be joined together using a variety of techniques. For example, the two pieces of the micro-needle device 100 can be joined using ultrasonic welding, heat sealing or a press fit (e.g., a friction fit). Alternatively, a thread connection or a medical grade chemical adhesive can be used to join the two pieces of the micro-needle device 100. Examples of such medical grade chemical adhesives include, but are not limited to, cyanoacrylates, epoxies, polyurethanes and silicones, as are known.

Figure 1D:
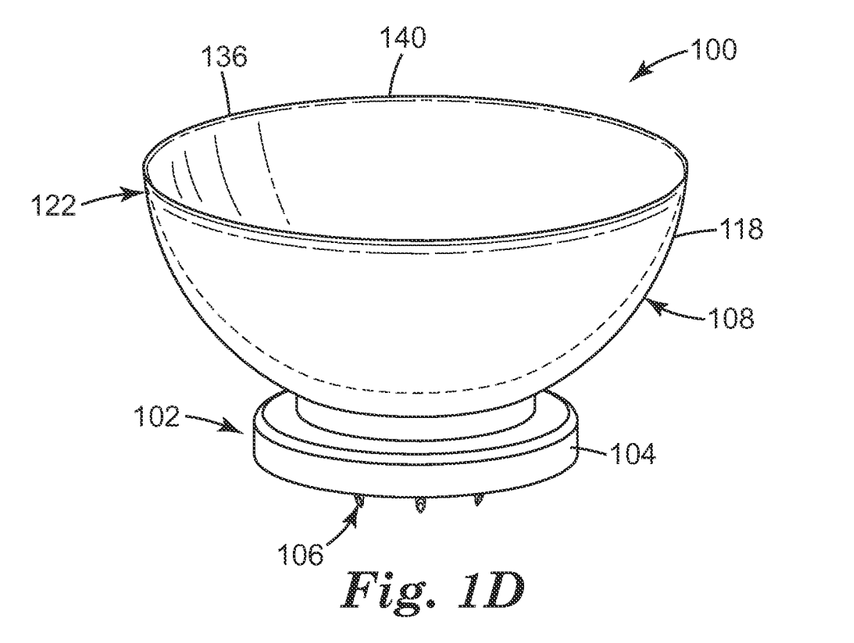
FIG. 1D is a perspective view of a micro-needle device according to an embodiment of the present disclosure.

As discussed herein, the exterior surface 126 of the base 104 provides a relatively large surface on which the doctor can both hold and apply force to the micro-needle device 100 to insert the micro-needles 106 in the oral tissue of the patient. Once inserted, the doctor can hold the micro-needle array 102 firmly against the oral tissue of the patient (e.g., using the thumb and the middle finger) while applying a compressive force to the outer surface 122 of the hollow spheroid shaped container 108 (e.g., with the index finger). As the compressive force is applied to the outer surface 122 of the hollow spheroid shaped container 108, the wall 118 elastically deforms. As this occurs, the outer surface 122 of the hollow spherical container 108 changes from having a convex shape (as illustrated in FIG. 1A and FIG. 1D to having a concave shape 140 (shown with a broken line in FIG. 1A) under the compressive force applied to the outer surface 122 of the hollow spheroid shaped container 108. So, as illustrated, the geometry of the hollow spherical container 108 changes under pressure from a user's finger from a first shape (e.g., a convex shaped) to an "inverted" state (e.g., a concave shape) that remains stable (e.g., does not move back towards the first shape) once the users finger is removed from the outer surface 122 of the hollow spheroid shaped container 108.

The outer surface 122 of the wall 118 can also include a volumetric scale marker 136. The volumetric scale marker 136 can take a variety of forms. For example, the volumetric scale marker 136 can be defined by a transition in a thickness 138 of the wall 118, where the thickness 138 of the wall 118 is measured perpendicular to the inner surface 120 and the outer surface 122 of the wall 118. As illustrated, the transition in the thickness 138 of the wall 118 follows along a latitudinal portion of the hollow spheroid shaped container 108. The transition in the thickness 138 of the wall 118 can help to provide the user with tactile feedback as to how much of the dental local anesthetic has been dispensed through the micro-needles 106 of the micro-needle array 102.

The volume 124 of the hollow spheroid shaped container 108 can be about one milliliter (ml). Other volumes are possible. The volumetric scale marker 136 can be used to provide indications of fractional amounts of the volume 124 that have been delivered as the compressive force is applied to the outer surface 122 of the hollow spheroid shaped container 108. For example, two of the volumetric scale markers 136 (as illustrated in FIGS. 1A and 1B) can be positioned to provide, for example, one-third (⅓) of a ml marks on the hollow spheroid shaped container 108. Other numbers of volumetric scale markers 136 can be used. Visual indicators can also be used, in addition to the changes in thickness 138, such as changes in color and/or shade of the outer surface 122 of the wall 118 at the volumetric scale markers 136.

In an additional embodiment, the micro-needle device 100 can also include a medical grade pressure sensitive adhesive located at least partially across the outer surface 122 of the wall 118. For example, the medical grade pressure sensitive adhesive can be located across the entirety of the outer surface 122 of the wall 118. The medical grade pressure sensitive adhesive can help to retain the micro-needle device 100 on a user's finger. Examples of suitable medical grade pressure sensitive adhesive include, but are not limited to, rubber or Acrylic ester copolymers, zinc oxide rubber adhesives and polyacrylate adhesives.

Figure 2A:
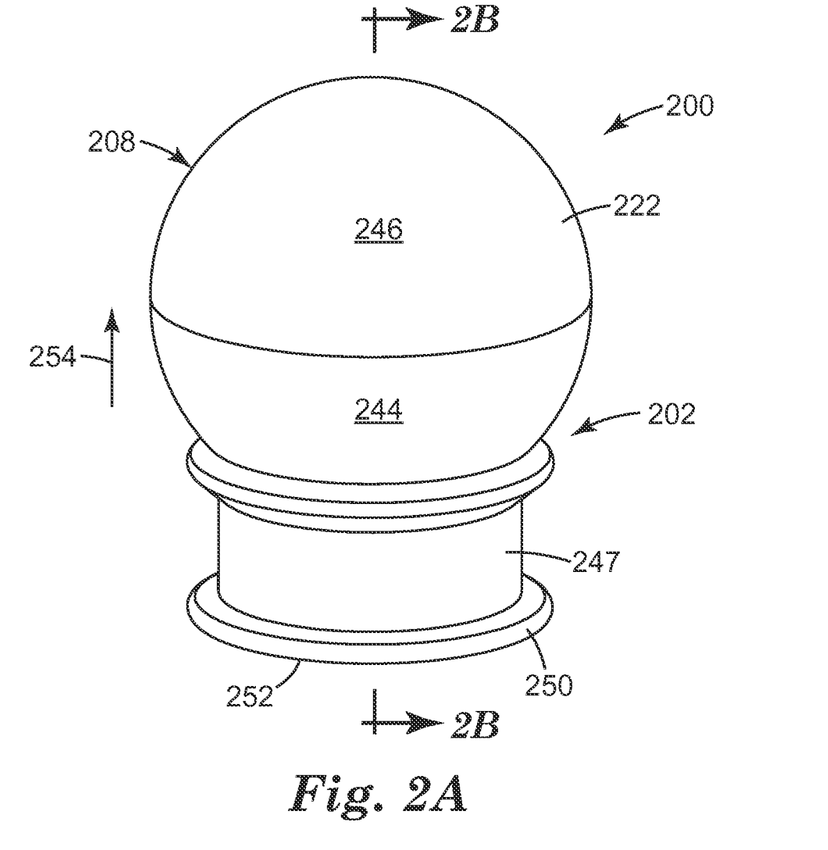
FIG. 2A is a perspective view of a micro-needle device according to an embodiment of the present disclosure.
Figure 2B:
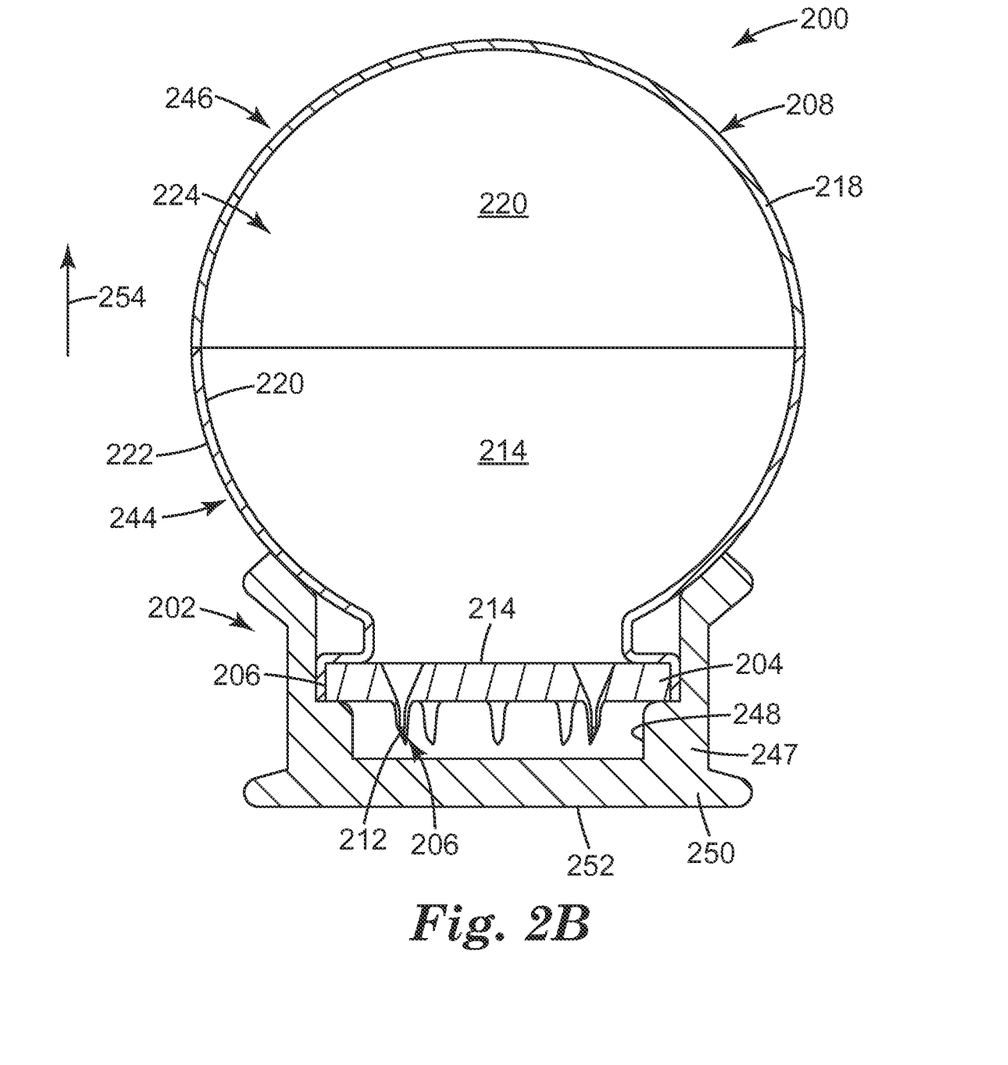
FIG. 2B is a cross sectional view of the micro-needle device taken along lines 2B in FIG. 2A.

Referring now to FIGS. 2A and 2B, there is shown an embodiment of the micro-needle device 200 according to the present disclosure. The micro-needle array 202 includes, as previously discussed, the base 204, two or more of an elongate micro-needle 206, and a hollow spheroid shaped container 208 at least partially defined by the outer surface 222 of the wall 218. As illustrated, the base 204 has an exterior surface 226 that defines the disk-shape of the micro-needle array 202.

FIGS. 2A and 2B also provide an embodiment of the micro-needle device 200 in which the first major surface 214 of the base 204 defines a first half 244 of the hollow spheroid shaped container 208 and the inside surface 220 of the wall 218 defines a second half 246 of the hollow spheroid shaped container 208. As discussed herein, the base 204 is formed of a polymer that is more rigid than the polymer used to form the wall 218 of the hollow spheroid shaped container 208. This configuration allows for a larger surface area on which to grip the micro-needle device 200. In addition this configuration helps to define the concave shape that the micro-needle device 200 will take once the dental local anesthetic is dispensed from the volume 224 defined by first major surface 214 of the base 204 and the inner surface 220 of the hollow spheroid shaped container 208 (e.g., the shape seen generally in FIG. 1D).

FIGS. 2A and 2B also provide an embodiment of the micro-needle device 200 that includes a removable cover 247 positioned over at least a portion of the base 204 and the two or more of the elongate micro-needle 206. The removable cover 247 can be releasably attached to the base 204 through a friction fit between the exterior surface 226 of the base 204 and an inside surface 248 of the removable cover 247. For example, the friction fit between the exterior surface 226 of the base 204 and the inside surface 248 of the removable cover 247 can be a conically friction fit. There can also be a retention rim or ridge that can releasably seat into or over a groove in the base 204. Alternatively, the removable cover 247 can be releasably attached to the base 204 through threaded surfaces, where the exterior surface 226 of the base 204 can have an external thread that engages and travels along an internal thread formed on the inside surface 248 of the removable cover 247.

The removable cover 247 can be formed of a polymeric material. Examples of such polymeric materials include, but are not limited to, those selected from the group consisting of high density polyethylene, low density polyethylene, polypropylene, polyethylene terephthalate, brominated butyl rubber or acrylonitrile-methyl acrylate copolymer. An example of the acrylonitrile-methyl acrylate copolymer includes BAREX®.

As illustrated, the inside surface 248 of the removable cover 247 is spaced apart from the elongate micro-needles 206 so that the two structures do not touch. The removable cover 247 also provides for a foot 250 having a planar surface 252. The planar surface 252 of the foot 250 allows the user to place the micro-needle device 200 in an upright position (shown by arrow 254) on a surface.

Figure 3:
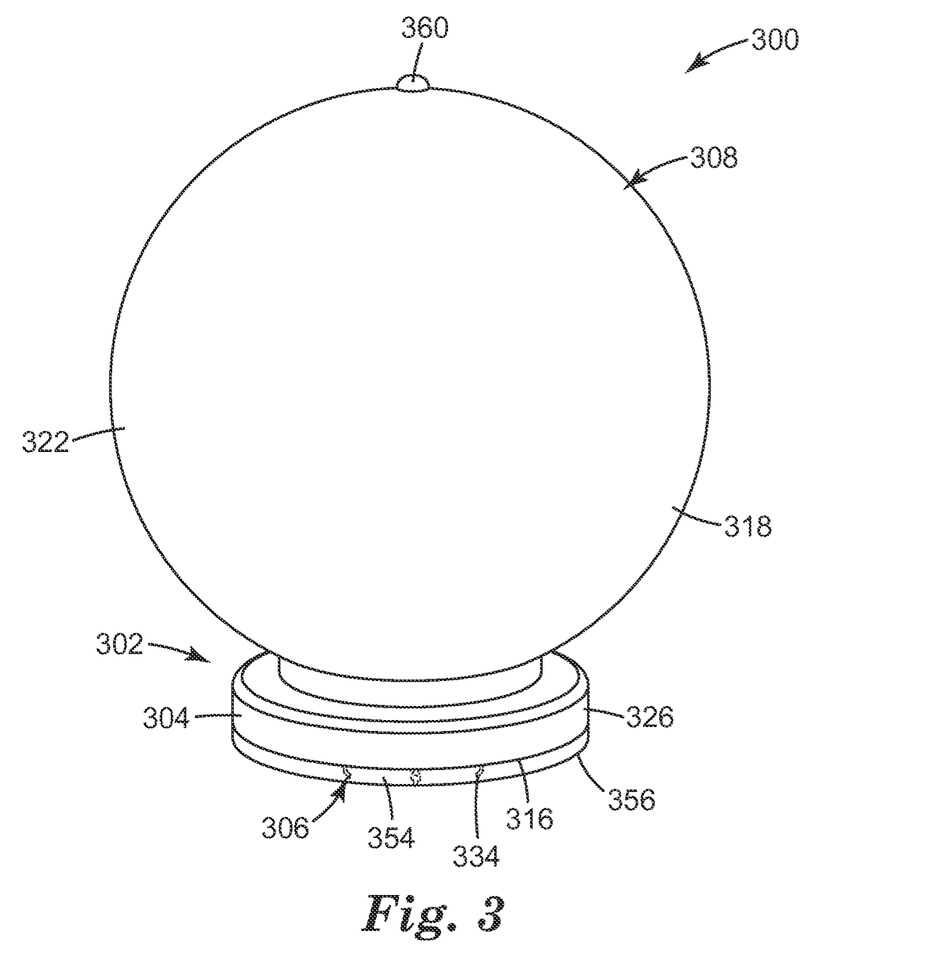
FIG. 3 is a perspective view of a micro-needle device according to an embodiment of the present disclosure.

Referring now to FIG. 3, there is shown an additional embodiment of the micro-needle device 300 according to the present disclosure. The micro-needle array 302 includes, as previously discussed, the base 304, two or more of an elongate micro-needle 306, and a hollow spheroid shaped container 308 at least partially defined by the outer surface 322 of the wall 318. As illustrated, the base 304 has an exterior surface 326 that defines the disk-shape of the micro-needle array 302.

As illustrated, the outer surface 322 of the micro-needle device 300 can include a surface marking 360 that can be both seen and felt (e.g., a palpable bump) by the user's finger at a location that is approximately the most distal from the second major surface 316 of the base 304. The outer surface 322 of the micro-needle device 300 can also include a concave portion (or other means of tactile geometrical "finger guide") for better centering the pressing (index) finger.

FIG. 3 further illustrates that the second major surface 316 of the base 304 can further include a compressible coat 354 that surrounds the micro-needles 306. The compressible coat 354 is formed from a foamed elastic material that is compressible. Examples of such a foamed elastic material include viscoelastic polyurethane foams and low-resilience polyurethane foams. The compressible coat can also be formed from foams of polystyrene, polypropylene, polyethylene or polymers of other vinyl monomers as are known.

The compressible coat 354 has an outer surface 356. As illustrated in FIG. 3, each tip 334 of the micro-needle 306 does not extend above the outer surface 356 of the compressible coat 354 when in its uncompressed state. The compressible coat 354 can change shape under a compressive force, allowing the micro-needles 306 to extend beyond the outer surface 356 of the compressible coat 354.

The micro-needle device 300 can also include a removable cover (element 247 as illustrated in FIG. 2 and as discussed above) positioned over at least a portion of the base 304, the two or more of the elongate micro-needles 306 and the compressible coat 354. Alternatively, a foil layer can be used to cover at least a portion of the base 304 and the two or more of the elongate micro-needles 306. The foil layer can also be used to cover at least a portion of the base 304, the two or more of the elongate micro-needles 306 and the compressible coat 354. The foil layer can be a single layer or a multilayer film having a thickness of 10 micro-meters (μm) to 50 μm. The foil layer can be formed from a polymer, such as PE, PP, PET and/or a metal such as aluminum.

The foil layer can remain on the micro-needle device 300 during its use with a patient, where the micro needles 306 pierce the foil layer as the micro-needle device 300 is used with the patient. So, for example, once the micro-needle device 300 is positioned in a patient's mouth the foil layer is in contact with the oral tissue of the patient. As pressure is applied to the base 304, the compressible coat 354 changes shape allowing the micro-needles 306 to pierce the foil layer and to contact the patient's oral tissue(s). The foil layer remains on the micro-needle device 300 when it is removed from the patient's mouth.

We claim:

1. A micro-needle device for delivering a dental local anesthetic, comprising:
    a micro-needle array having a base and two or more of an elongate micro-needle, the elongate micro-needle having an interior surface defining an opening through the elongate micro-needle and the base having a first major surface and a second major surface through which the opening of the elongate micro-needle passes to provide a passage across the base, the base further comprising a sidewall extending between the first major surface and the second major surface thereof; and
    a hollow spheroid shaped container comprising a wall with a first wall portion and a second wall portion wherein the second wall portion has a wall thickness less than a wall thickness of the first wall portion,
    wherein an inner surface of the first wall portion contacts and fluidly seals against the first major surface of the base, and where the first wall portion extends over the sidewall on the base such that an exterior surface of the base forms a gripping surface against which force may be applied to retain the micro-needle device and insert the micro-needle array into an oral tissue, and
    where the first major surface of the base and an inner surface of the wall of the hollow spheroid shaped container define a volume that is in fluid connection with the opening of the elongate micro-needle to allow the dental local anesthetic to flow from the volume of the micro-needle device through the opening of the elongate micro-needle when the hollow spheroid shaped container is elastically deformed under a compressive force applied to an outer surface of the wall of the hollow spheroid shaped container and wherein the outer surface of the wall of the hollow spheroid shaped container comprises a volumetric scale marker defined by a transition in a thickness of the wall between the first wall portion and the second wall portion thereof.

2. The micro-needle device of claim 1, where the transition in the thickness of the wall follows along a latitudinal portion of the hollow spheroid shaped container.

3. The micro-needle device of claim 1, where the wall of the hollow spheroid shaped container is formed of a polymer.

4. The micro-needle device of claim 3, where the polymer is selected from the group consisting of high density polyethylene, low density polyethylene, polypropylene, polyethylene terephthalate, brominated butyl rubber or acrylonitrile-methyl acrylate copolymer.

5. The micro-needle device of claim 1, where an outer surface of the second wall portion changes from having a convex shape to having a concave shape under the compressive force.

6. The micro-needle device of claim 1, where the volume of the hollow spheroid shaped container is about one milliliter.

7. The micro-needle device of claim 1, where the base of the micro-needle array has a disk-shape.

8. The micro-needle device of claim 7, where the base of the micro-needle array in the disk-shape has a diameter of 4 millimeters (mm) to 15 mm and a height of 0.5 mm to 8 mm.

9. The micro-needle device of claim 7, where the base of the micro-needle array has 6 to 18 micro-needles.

10. The micro-needle device claim 9, where the elongate micro-needle is uniformly arranged in a circular pattern to define the infiltration area.

11. The micro-needle device of claim 1, wherein the outer surface of the wall of the hollow spheroid shaped container includes a pressure sensitive adhesive for retaining the micro-needle device on a user's finger.

\* \* \* \* \*